(12) United States Patent
Lu et al.

(10) Patent No.: US 7,312,071 B2
(45) Date of Patent: Dec. 25, 2007

(54) EFFECTIVE MONITORING SYSTEM FOR ANTHRAX SMALLPOX, OR OTHER PATHOGENS

(75) Inventors: Peter S. Lu, Mountain View, CA (US); Thomas M. Sherlock, Los Altos, CA (US); Joseph Byerly, Pebble Beach, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 539 days.

(21) Appl. No.: 10/313,354

(22) Filed: Dec. 6, 2002

(65) Prior Publication Data

US 2003/0153021 A1   Aug. 14, 2003

Related U.S. Application Data

(60) Provisional application No. 60/337,190, filed on Dec. 6, 2001.

(51) Int. Cl.
*C12M 1/34* (2006.01)

(52) U.S. Cl. .................. 435/287.6; 435/287.4; 435/808; 435/288.3; 435/288.5; 73/61.63; 73/863.23

(58) Field of Classification Search ............. 435/287.6, 435/287.4, 808, 288.3, 288.5; 73/863.23, 73/61.63
See application file for complete search history.

(56) References Cited

U.S. PATENT DOCUMENTS

| | | | | |
|---|---|---|---|---|
| 4,596,773 A | * | 6/1986 | Wheeler, Jr. ................. | 435/31 |
| 5,736,355 A | * | 4/1998 | Dyke et al. ............... | 435/287.6 |
| 5,773,234 A | * | 6/1998 | Pronovost et al. .......... | 435/7.36 |
| 5,919,356 A | * | 7/1999 | Hood ........................... | 210/85 |
| 6,180,395 B1 | * | 1/2001 | Skiffington et al. ....... | 435/287.6 |
| 6,334,980 B1 | * | 1/2002 | Hayes et al. ................ | 422/68.1 |
| 6,599,715 B1 | * | 7/2003 | Vanderberg et al. .......... | 435/34 |
| 7,060,223 B2 | * | 6/2006 | DiCesare et al. ............. | 422/52 |
| 2002/0076804 A1 | * | 6/2002 | Sheppard et al. ........ | 435/287.1 |

* cited by examiner

*Primary Examiner*—Gladys J P Corcoran
*Assistant Examiner*—Nathan A. Bowers
(74) *Attorney, Agent, or Firm*—Townsend and Townsend and Crew, LLP

(57) ABSTRACT

A device and method for detecting anthrax or other pathogens are disclosed. Individual self-contained monitoring devices of a monitoring system can be portable or stationary (e.g. installed in air ducts or plumbing of buildings) and can be part of a network of devices. Monitoring devices may be used for the detection of a variety of airborne or surface pathogens, including but not limited to anthrax, smallpox, and Salmonella. Bioamplification-coupled proteomics assays provide rapid and reliable detection of pathogens, with self-checking capabilities reducing or eliminating false positives and false negatives. Sample preservation capability allows pathogen samples to be preserved after detection for further testing. The device of the invention can be remotely operated by minimally trained technicians or security personnel. The pathogen monitoring device of the invention provides a more compact, accurate, rapid, and cost-effective alternative to other anthrax detectors, and an effective weapon against bioterrorism.

1 Claim, 12 Drawing Sheets

Assembled Unit

Cross-section - sampling "OPEN" position

Cross-section - sealed position

Cross-section - Sample Prep. Begins

Detection system - "pregnancy" sandwich ELISA

Remote Anthrax Detector

Cartridge for manual machine

Manual machine

Heater
Seal breaker

EFFECTIVE MONITORING SYSTEM FOR ANTHRAX SMALLPOX, OR OTHER PATHOGENS

CROSS-REFERENCES TO RELATED APPLICATIONS

This application claims priority to provisional application No. 60/337,190, filed Dec. 6, 2001.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

The rapid detection of microorganisms, particularly highly virulent pathogens, is required for the timely treatment of serious infections. Contamination of air or water by pathogenic microorganisms can occur naturally, can be the result of unintended human interference, or can occur as a result of intentional use of biological warfare agents against military and civilian populations. Because of the ability of pathogens to disseminate and infect human populations rapidly, a detection system requires speed, versatility and, preferably, portability. Early detection and identification of pathogens in patients allows a health care worker to diagnose and appropriately treat a patient. Remote sampling and detection of microorganisms can limit exposure to biological agents through the identification of contaminated areas. These areas can then be quarantined and decontaminated by appropriately trained individuals.

However, in spite of the need for rapid detection of pathogens, detection equipment in current use has significant shortcomings. Manipulating and interpreting pathogen detection devices in the field is a hazardous duty, and can be made more difficult by cumbersome protective clothing worn by health care or military personnel. Thus, remote and automated sensing is required to address both safety and efficiency concerns. To be truly effective as a monitoring system, it also must be widely distributed, such that detection of bioterrorism induced or natural outbreaks can be rapidly identified and controlled. In turn, the need for a widespread early warning network demands that any detection device be accurate, automated and relatively inexpensive.

There are several methods commonly used to detect pathogens in collected samples, but not all of these methods are rapid, readily automatable or of low cost. These include (i) amplification of pathogen-specific nucleic acid sequences, including methods for amplifying pathogen-specific nucleic acid sequences requiring numerous time-consuming steps that are difficult to automate and often produce false positives or false negatives; (ii) culture of pathogens on appropriate growth media, followed by isolation and either time-consuming biochemical or histological assays; (iii) mass spectrometer-based detection of pathogen-specific components, in which each detection unit is expensive to produce; and (iv) serological-based assays, which have limited sample size and can only detect pathogens in an infected individual.

There are several disadvantages to these methods. Nucleic acid amplification and many examples of biochemical assays require a method of breaking open the cell and isolating the components. The techniques used to break open the cell have been shown to make these assays difficult to reproduce and inaccurate (Dang et al., 2001, Appl Environ Microbiol 67(8):3665-70). Culturing pathogens on solid growth media can take several days, in which time an infected patient could die or be seriously compromised. Mass spectrometry, although accurate, requires larger sample sizes, high trained operators, and a very expensive testing unit.

One general class of methods in common use for pathogen detection, enzyme-linked immunosorbent assays (ELISAs), can be made automatable, rapid and inexpensive. With regard to the latter, low cost provides multiple monitoring device capability. However, ELISAs are not very sensitive, and incapable of detecting small numbers (e.g., 1-10 anthrax spores) of pathogens. The method of the present invention combines the cost-efficiency and rapidity of an ELISA-based "dipstick" assay with the increased sensitivity of bioamplification. In this manner, the method of the invention is able to accurately and rapidly detect very small amounts of pathogens in airborne, fluid, or surface samples. The simplicity and accuracy of this protein amplification assay imparts the ability to produce relatively simple and portable detection devices.

In the case of Anthrax, treatment is effective if initiated within 72 hours of infection. This means that samples must be analyzed in time to identify potentially infected individuals and begin treatment. The invention discloses a device that takes advantage of this latency period to improve on the accuracy of an inexpensive test, significantly reducing false positive and false negative results using bioamplification. This method and device for detection of pathogens such as Anthrax can give automated and accurate pathogen detection within 12-24 hours, leaving plenty of time to begin treatment for infected individuals.

SUMMARY

The present invention provides a device for detection of pathogens at one or more locations. In one aspect, the invention provides stationary or portable devices for collecting either surface or airborne samples and determining the presence or absence of pathogens. In one embodiment, stationary detection devices can be permanently installed in air ducts for ongoing monitoring of airborne microorganisms. In another embodiment, portable devices may be used to selectively monitor areas suspected of being targets of biological warfare. In another aspect, the invention discloses a network of collection and detection units for monitoring pathogens and potential outbreaks. Each detection unit can be either in proximity to an assay analyzer or remotely removed from the analyzer. A single test cartridge includes a sample chamber and a test chamber separated by a breakable seal. The sample chamber can be either a fluid intake through which a fluidic substance, such as a gas or liquid, enters the system, or a receptacle for receiving a, specimen swab, which is immersed in a fluid for suspending microorganisms.

In another aspect, the invention provides a sealable cartridge for detecting elements of microorganisms, comprising (i) a sample chamber, wherein a test sample is suspended in fluid; (ii) a test chamber, wherein the fluid is tested for elements of a microorganism; and (iii) a breakable seal between the sample and test chambers. Some sealable cartridges further comprise a detection means. Some sealable cartridges further comprise a transmission means. Some sealable cartridges further comprise an assay analyzer. With some such sealable cartridges, the microorganism is *Bacillus anthracis*.

In another aspect, the invention further provides a pathogen monitoring system for detecting pathogens, comprising: an intake or receptacle through which a fluid or gas enters said pathogen monitoring system or is added to said pathogen monitoring system; a means for drawing or pushing said fluid or gas into said pathogen monitoring system and through a conduit connectively communicating with said intake; a filtering means within said conduit through which said fluid or gas passes and retains microorganisms present in said fluid or gas; a medium reservoir for a growth medium on a side of said filtering means opposite from said intake or receptacle, wherein said growth medium passes through said filtering means and removes said micrornaisms from said filtering means. Some pathogen monitoring systems further comprise a detection means. Some pathogen monitoring systems further comprise a transmission means. Some pathogen monitoring systems further comprise an assay analyzer. With some pathogen monitoring systems, the microorganism being monitored is *Bacillus anthracis*. In one embodiment, the pathogen monitoring system may be used for the detection of microorganisms being used or suspected of being used for bioterrorism.

In another aspect, the invention further provides a pathogen monitoring system for detecting microorganisms, comprising: an intake or receptacle through which a fluid or gas enters said pathogen monitoring system or is added to said pathogen monitoring system; a means for drawing or pushing said fluid or gas into said microbial monitoring system and through a conduit connectively communicating with said intake; a filtering means within said conduit through which said fluid or gas passes and retains microorganisms present in said fluid or gas; an exhaust chamber, wherein said filtering means is interposed between said intake and said exhaust chamber; a medium reservoir on a side of said filtering means opposite said retained microorganisms, comprising a growth medium and a reservoir breakable seal; a plunger means, wherein pressure placed on said plunger means: (i) engages a hermetic seal between said medium reservoir said filtering means; (ii) breaks said reservoir breakable seal and forces growth medium through said filtering means in a direction opposite of flow of said fluid or gas; and (iii) backwashes said microorganisms from said filtering means and suspends said microorganisms in said growth medium; an incubation chamber for incubating and growing said microorganisms; a programmable temperature-regulating means for controlling the temperature of said incubation chamber; an incubation chamber breakable seal through which said growth medium passes into a test chamber for detecting said microorganisms; a timer for controlling intervals between assay measurements; a detection means within said test chamber; wherein said detection means determines the presence or absence of said microorganisms without killing said microorganisms or inhibiting said growing; and a transmission means; wherein said presence or absence of said microorganisms is reported via said transmission means to an assay analyzer. The simplicity of the device and the use of a simple positive or negative (i.e. presence or absence) result allows the user to effectively operate the device with little training, thereby reducing operating costs.

With some pathogen monitoring systems, the transmission means is a wire connection, a radio link, a microwave transmission, an infrared transmission, a cellular phone, or a computer network. With some pathogen monitoring systems, the pathogen monitoring system comprises a network of separate monitoring devices. With some such pathogen monitoring systems, the assay analyzer is remote from said pathogen monitoring system and said reporting relays location of a pathogen monitoring device to said assay analyzer. With some such pathogen monitoring systems, the location is determined by a global positioning system. With some pathogen monitoring systems, the detection means is selected from the group consisting of an enzyme immunoassay, an optical immunoassay, mass spectroscopy, and gene sequence analysis. With some such pathogen monitoring systems, the enzyme immunoassay comprises an immunoassay strip that wicks the growth medium past a detection area and a control area on said detection strip.

With some microbial monitoring systems, the microorganisms being monitored are selected from the group comprising of *Bacillus anthracis, Yersinia pestis, Neiserria menigitidis, Coxiella burnettii, Coccidiodes immitis, Francisella tularensis, Cryptococcosis neofomans, Escherichia coli, Haemophilus influenzae, Brucella* species, *Salmonella* species, *Shigella* species, *Chlamydia psittaci, Vibrio cholerae, Staphylococcus enterotoxin B, Histoplasma capsulatum, Rickettsia* species, *Corynebacterium diphtheriae, Burkholderia pseudomallei, Burkholderia mallei, Mycobacterium tuberculosis, Blastomyces dermatitidis,* and *Nocarida* species.

With some pathogen monitoring systems the pathogen monitoring system comprises an optical sensor for determining assay results. With some pathogen monitoring systems, the pathogen monitoring system comprises a variable timer that determines the frequency of detection assays. With some pathogen monitoring systems, the pathogen monitoring system comprises a detection unit comprising a disposable cartridge. With some such pathogen monitoring systems, the disposable cartridge is moved in automated fashion into place for incubation and assay determination, the detecting is conducted automatically, and the disposable cartridge is automatically removed to a waste chamber after said detecting. With some pathogen monitoring systems, the plunger means comprises a bladed or pointed edge for releasing said growth medium. With some pathogen monitoring systems, the programmable temperature-regulating means elevates the temperature of the microbial monitoring system to shock bacterial endospores and initiate endospore germination.

In another aspect, the invention further provides a pathogen monitoring system for detecting microorganisms, comprising: a network of pathogen monitoring devices reporting to a remote assay analyzer, wherein each of said pathogen monitoring devices comprises at least one disposable cartridges comprising: an intake or receptacle through which a fluid or gas enters said pathogen monitoring system or a swab is deposited within said pathogen monitoring system in a fluid; a means for drawing or pushing said fluid or gas into said pathogen monitoring system and through a conduit connectively communicating with said intake or receptacle; a semipermeable membrane within said conduit through which said fluid or gas passes and which retains microorganisms present in said fluid or gas; an exhaust chamber, wherein said semipermeable membrane is interposed between said intake and said exhaust chamber; a medium reservoir containing growth medium on the side of said semipermeable membrane opposite said retained microorganisms; a plunger means comprising a bladed or pointed edge for releasing said growth medium; wherein depressing said plunger means: (i) engages a hermetic seal between said medium reservoir said semipermeable membrane; (ii) forces growth medium through said semipermeable membrane in a direction opposite of flow of said fluid or gas; and (iii) backwashes said microorganisms from said semipermeable membrane and suspends said microorganisms in said growth medium; a breakable seal through which said growth medium passes into a test chamber for incubating and growing said microorganisms; a timer for determining intervals between immunoassay measurements; a temperature-regulating means that maintains said test chamber at a temperature that promotes growth of at least one target microorganism; an immunoassay test strip within said test chamber; wherein said immunoassay strip wicks said growth medium past a detection area on said detection strip, said detection area comprises an indicator assay region and a control assay region; and said immunoassay test strip determines the presence or absence of said at least one target microorganism, wherein said presence or absence of said at least one target microorganism is reported with location of said microbial monitoring device to said remote assay analyzer.

In another aspect, the invention further provides a method for detecting pathogens in an air or fluid specimen, comprising: passing an air or gas specimen or a specimen derived from a swab through a pathogen monitoring system, wherein the pathogen monitoring system comprises an intake or receptacle through which a fluid or gas enters said pathogen monitoring system or is added to said pathogen monitoring system; a means for drawing or pushing said fluid or gas into said pathogen monitoring system and through a conduit connectively communicating with said intake; a filtering means within said conduit through which said fluid or gas passes and retains microorganisms present in said fluid or gas; a medium reservoir for a growth medium on a side of said filtering means opposite from said intake or receptacle, wherein said growth medium passes through said filtering means and removes said microorganisms from said filtering means; retaining microorganisms within said air or fluid specimen on a filtering means within said pathogen monitoring system; incubating said microorganisms with a growth medium in said pathogen monitoring system at temperature that promotes growth of at least one target microorganism; and determining presence or absence of said at least one target microorganism with a detection means within said pathogen monitoring system; where determination of the absence of said at least one target microorganism initiates a subsequent round of incubation and determining.

In another aspect, the invention further provides a kit for detecting pathogens, comprising: at least one disposable cartridge for use in a pathogen monitoring system, wherein the pathogen monitoring system comprises an intake or receptacle through which a fluid or gas enters said pathogen monitoring system or is added to said pathgoen monitoring system; a means for drawing or pushing said fluid or gas into said pathogen monitoring system and through a conduit connectively communicating with said intake; a filtering means within said conduit through which said fluid or gas passes and retains microorganisms present in said fluid or gas; a medium reservoir for a growth medium on a side of said filtering means opposite from said intake or receptacle, wherein said growth medium passes through said filtering means and removes said microorganisms from said filtering means; and a sterile container for retaining said at least one disposable cartridge.

DETAILED DESCRIPTION OF THE INVENTION

I. General

Figure 1:
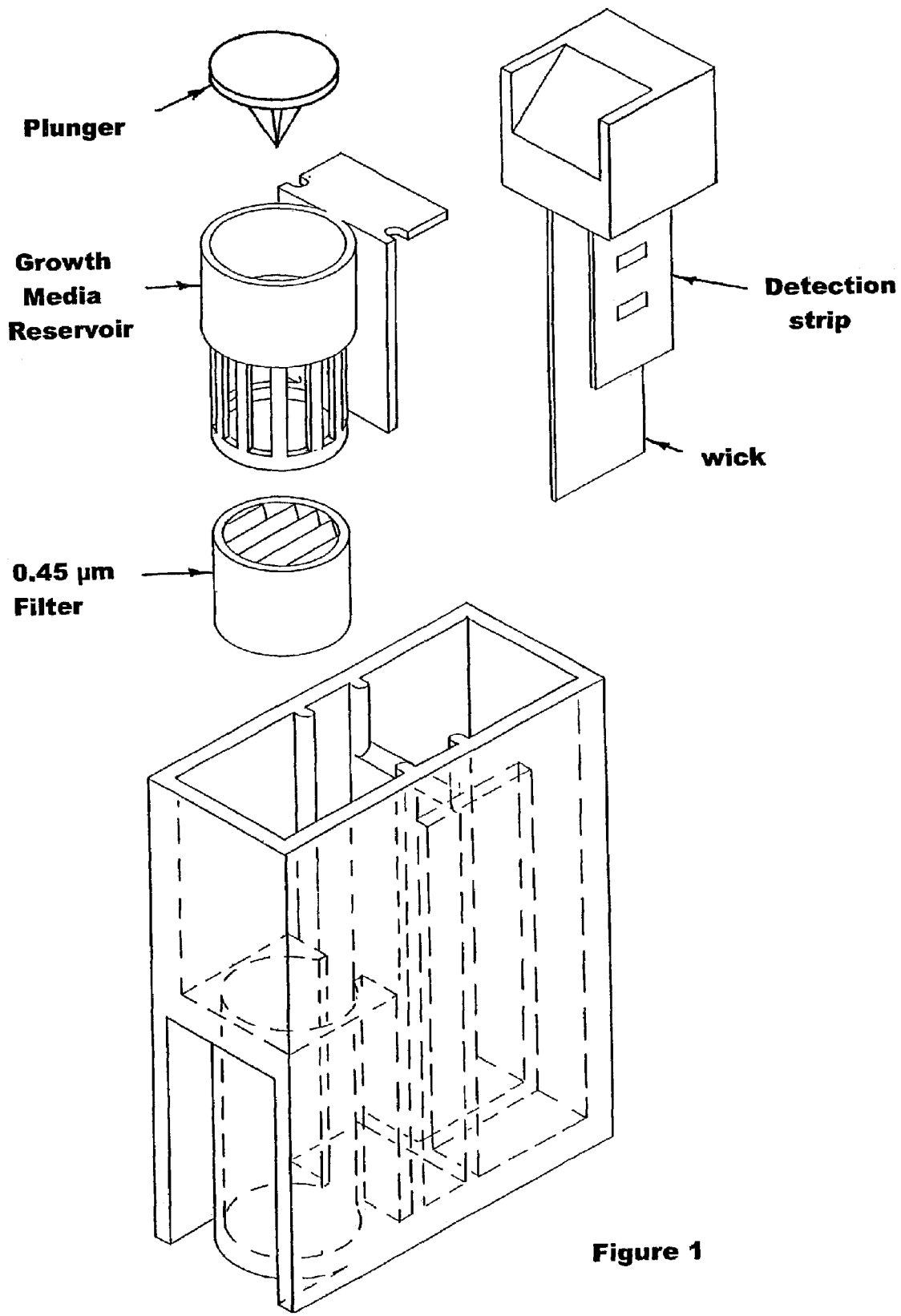
FIG. 1 shows an exploded view of one embodiment of a test cartridge.
Figure 2:
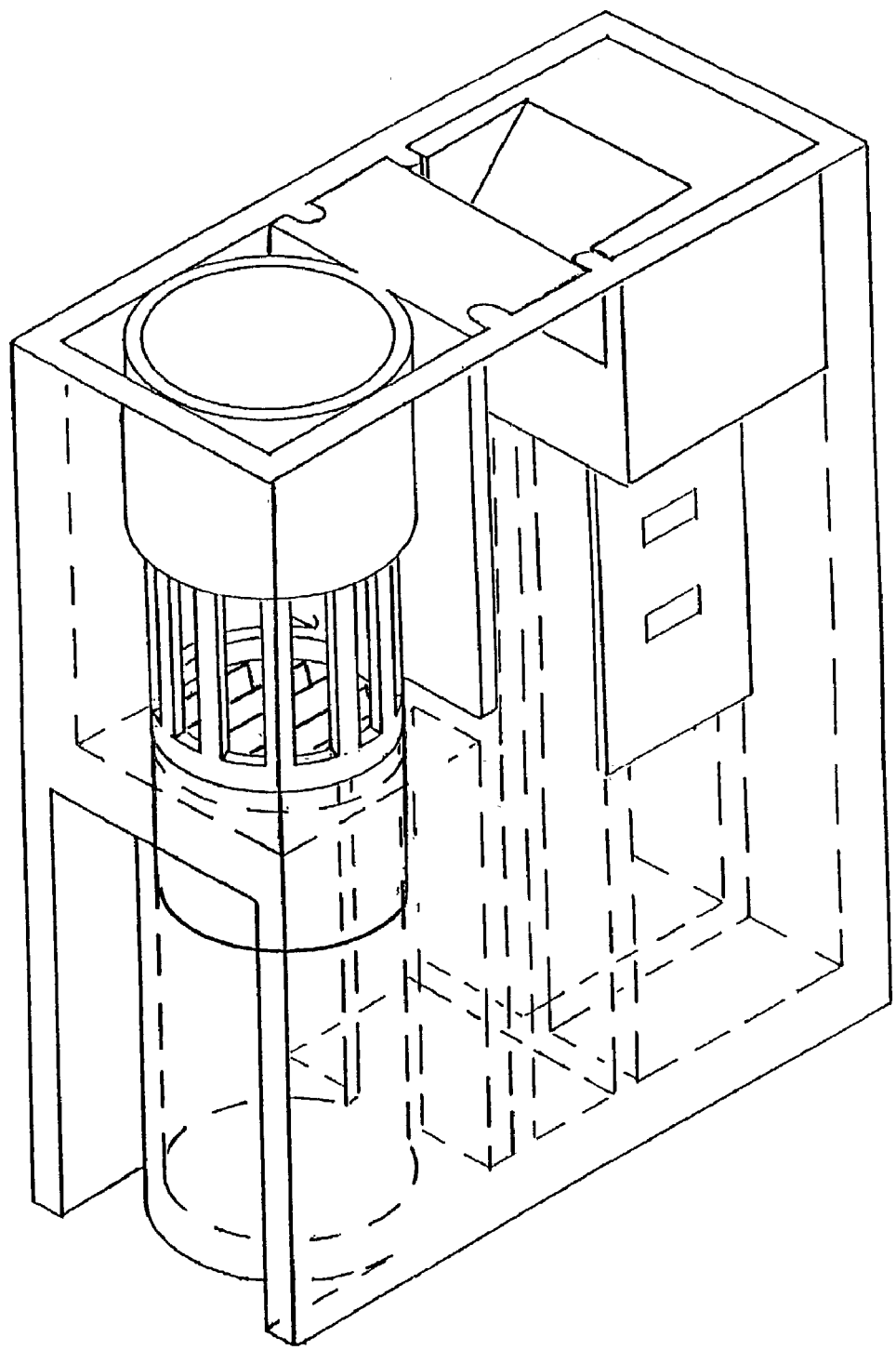
FIG. 2 shows an assembled view of the test cartridge.

The terms "fluid" or "fluidic substance" as used herein refers to any fluid, including air, a gas, or a liquid, including water and an aqueous solution.

The term "target microorganism" as used herein refers to a particular microorganism that one wishes to detect in a fluid sample. Target microorganisms can include pathogens, including bacterial, protozoal, viral, and fungal pathogens. Target microorganisms can be, naturally, accidentally, or intentionally introduced into a medium, such as air or a liquid plumbing system or reservoir, from which the fluid sample is derived. Target organisms can include those found in clinical settings that can cause nosocomial infections, such as *Enterobacteriaceae, Pseudomonas* species, *Streptococcus* species, and *Staphylococcus* species, and can include biowarfare agents and potential biowarfare agents. Examples of biowarfare agents or potential biowarfare agents include *Bacillus anthracis, Burkholderia mallei, Burkholderia pseudomallei, Brucella* species, *Chlamydia*

*psittaci, Corynebacterium diphtheriae, Coxiella burnettii, Cryptococcosis neofomans, Escherichia coli, Francisella tularensis, Haemophilus influenzae, Mycobacterium tuberculosis, Neiserria menigitidis, Rickettsia* species, *Salmonella* species, *Shigella* species, *Staphylococcus* species, *Streptococcus* species, *Vibrio cholerae*, and *Yersinia pestis*. Target microorganisms can also include fungal pathogens that can be naturally present in an environment, or intentionally introduced as biowarfare agents. Examples of the, latter include *Blastomyces dermatitidis, Coccidiodes immitis, Histoplasma capsulatum*, and *Nocarida* species. "Elements" of a microorgnaism include, but are not limited to, proteins, nucleic acids, secreted toxins, and alike, of a microorganism. "Elements" of a microorganism can also include any identifiable feature of a microorganism.

The term "monitoring device" refers to a single unit that can be fixed or portable, is programmable with respect to fluid sampling and assay parameters, and which contains the components necessary to determine the presence of microorganisms. The components include a power supply (if the unit is portable), a sampling station, one or more test cartridges, control and test result sensing elements.

The terms "microbial monitoring system" and "pathogen monitoring system" refers to one or more monitoring devices. If more than one monitoring device is used, they can be linked in a network that provides detection data to a single assay analyzer.

The term "detection unit" refers to a device for manipulation of test cartridges and sensing results of test cartridge assays. Detection unit can be used interchangeably with "monitoring device".

The terms "growth medium" and "growth media" refer to a mixture of nutrients that will support the growth of the target microorganism. This can include vitamins, minerals, salts, proteins, nucleic acids, yeast extracts, bacterial extracts and appropriate cells to allow growth of parasitic or pathogenic microorganisms.

The term "test cartridge" refers to a sealable chamber that includes a means for suspending a sample in liquid (sample chamber), a chamber with a detection strip or similar means to assay for the presence of a microbial element (test chamber), and a breakable seal between said elements.

The term "monitoring device" can refer to a detection unit or plurality of detection units.

The term "assay analyzer" refers to the test result-sensing unit of the monitoring device or a plurality of sensing units.

The term "pathogen" refers to any biological organism that can be propagated in humans or animals.

II. Overview

The invention is a monitoring system for detecting the presence of pathogens, including pathogenic microorganisms that can be present in an airborne, fluidic, or surface sample. The device comprises a sealable cartridge for sample collection and testing, and test result sensing unit. The device also comprises at least one element for reporting the test results. Multiple device units can constitute a network of devices reporting to a centralized location.

Each monitoring device further comprises at least one detection unit. The detection unit can comprise a test cartridge that can be disposable. Each monitoring device can also comprise multiple detection units. One or more detection units can be placed either in proximity to an assay analyzer, which is able to evaluate data from one or more detection units, or can be remotely removed from the analyzer. The evaluation of the data transmitted to the assay analyzer includes an assessment of whether one or more target microorganisms are present in a sample of a fluid.

The invention finds use in hospitals, laboratories or other buildings where pathogenic microorganisms can be present in, for example, air, plumbing, water specimens or water sources to which pathogenic microorganisms can be accidentally or intentionally introduced. The low cost, short time to assay results, the potential portability and the wide variety of pathogens that can be detected with the present invention allows a large number of monitoring devices to be used over a wide area for comprehensive detection capability.

In one embodiment, the invention may be used in areas suspected of being targets for bioterrorism. Stationary monitoring devices of the invention may be installed in air ducts or plumbing of buildings that may be targets of biological warfare (e.g. post offices, government offices, heavily populated builings) to constantly monitor levels of pathogens that may be used as biological weapons (e.g. anthrax). Portable monitoring devices may be used at multiple locations to monitor levels of pathogens in a wide region.

The invention may be operated remotely and results may be transmitted to a remote location, such that operators of the device will not risk exposure to the pathogen in the course of monitoring. This reduces cost significantly by eliminating the need for costly biological hazard teams and equipment currently used to enter potentially contaminated areas and detect the presence of pathogens at those locations.

III. Exemplary Monitoring Devices

One advantage of the presently disclosed monitoring system is the programmable nature of the system. The amount of fluid that enters the monitoring system, the temperature of incubation, the duration of incubation, the number of detection assays performed, and, optionally, the duration and temperature for "heat-shocking" bacterial endospores are all controllable parameters that can be programmed in advance or altered once a fluid has entered the monitoring device. The monitoring system is also versatile, in that it can be used to detect microorganisms in a gas, such as air, in a fluid, such as a water specimen, or obtained from a sample swab that has been wiped across a surface. A single monitoring device can be used to perform a plurality of assays, with either one specimen tested multiple times, or a number of fluid specimens tested. Another advantage of the present monitoring system is that the disclosed devices can be remote from a single assay analyzer that is used to report assay results. Another advantage includes the ability to link separate and remote monitoring devices in a network, thus providing the ability to detect target microorganisms across a selected region.

Figure 3:
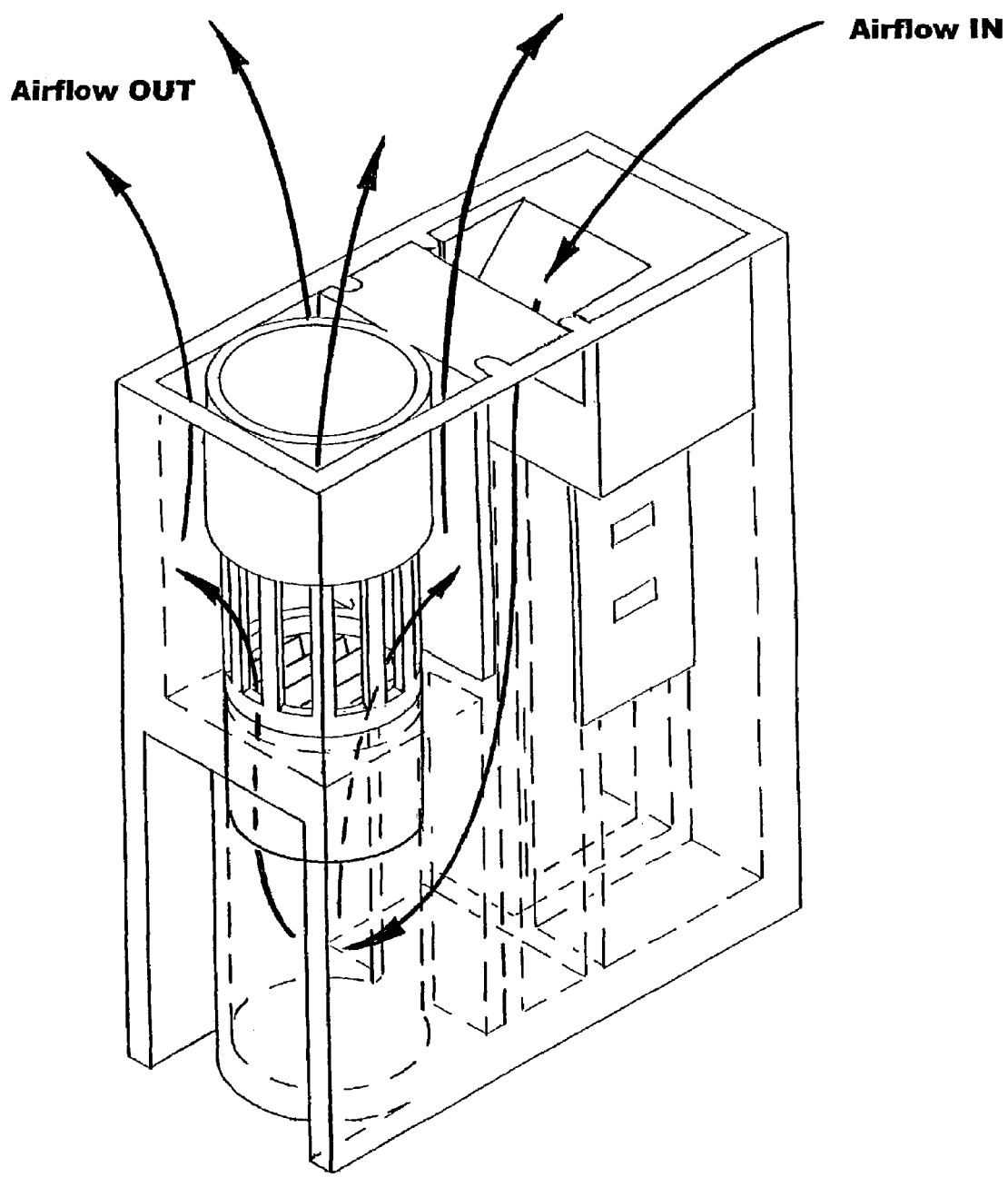
FIG. 3 shows the path of airflow through the test cartridge.
Figure 4:
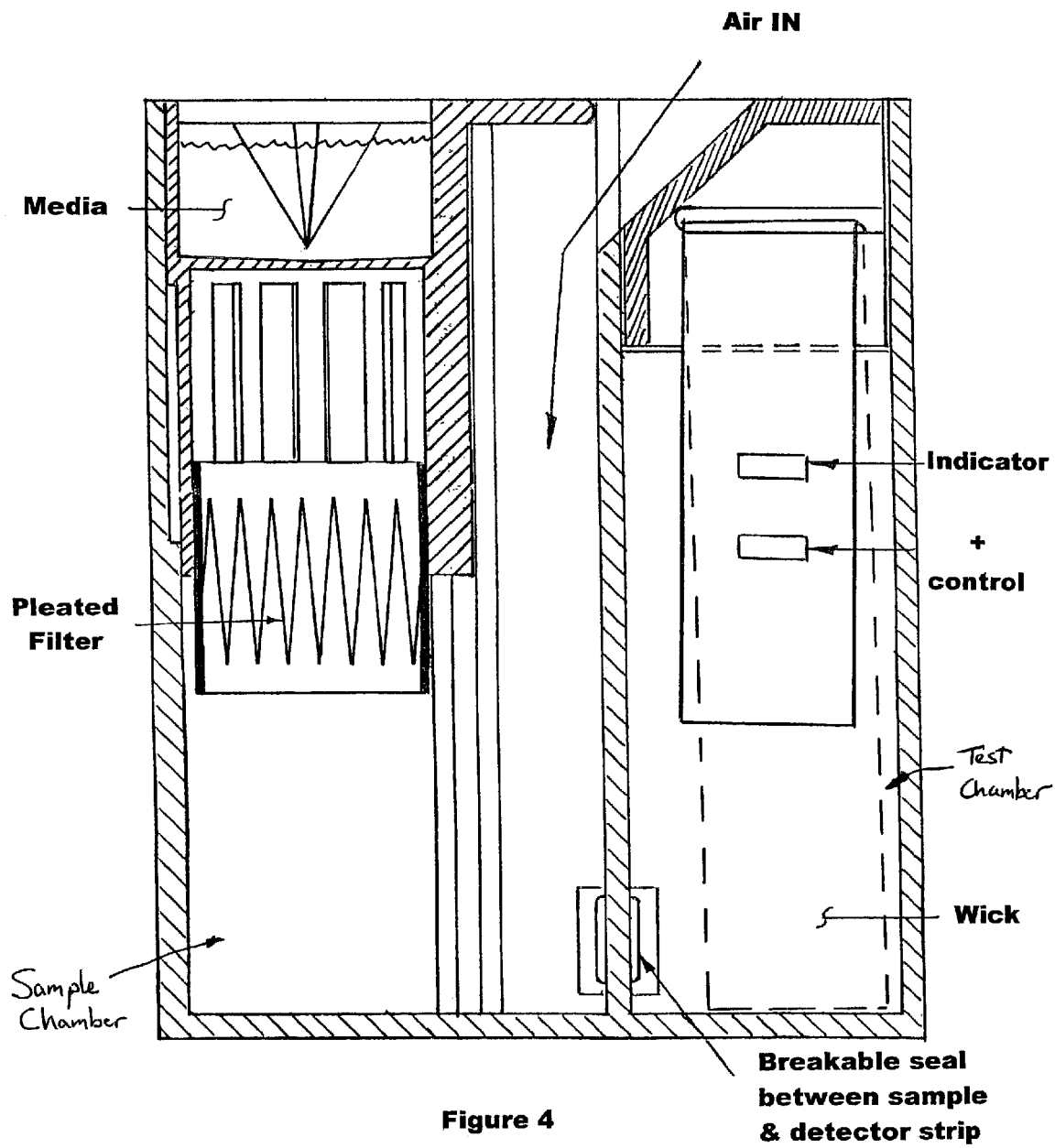
FIG. 4 shows a cross section of the test cartridge in sampling position.
Figure 9:
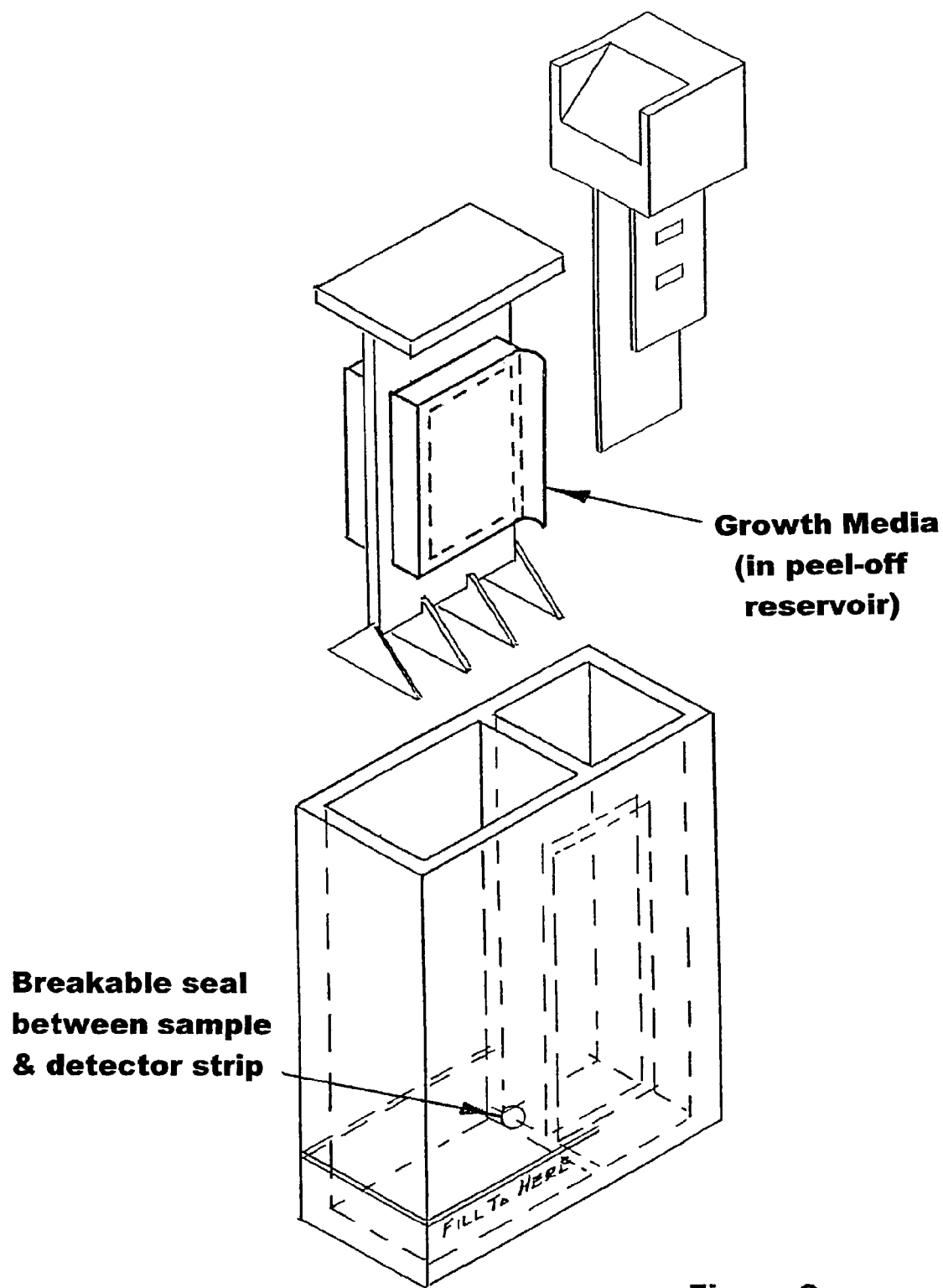
FIG. 9 shows an exploded view of a different embodiment of the test cartridge for use with manually loaded swabs.

A single detection unit includes a sample chamber and a test chamber separated by a breakable seal (FIGS. 4 and 9). The sample chamber includes either a fluid intake through which a fluid enters the detection unit, or a receptacle for receiving a sample swab used for surface testing. The ability of the unit to be adapted to airborne, fluidic, or surface pathogens provides a distinct advantage over other microorganism detectors. In the latter case, a suspending fluid is added to the receptacle to suspend microorganisms, including target microorganisms, which can be present on the swab (FIG. 9). Movement of the fluid into the sample chamber of the test cartridge can be generated by pressure, vacuum, electrokinetics, capillary action, gravity, manual actions or a combination thereof. Gas specimens are preferably drawn into the fluid intake by a vacuum pump located at or near and operably connected to an outlet of the test cartridge (FIG. 3). In the embodiment for gas or fluid samples, the fluid passes from the intake e through a conduit that leads to a filtration means, which can include a semipermeable membrane (FIGS. 3 and 4). A semipermeable membrane used in the present invention is of sufficient pore size and density such that the membrane retains microorganisms present in the fluid but also allows the fluid to pass through the membrane at an acceptable flow rate. The membrane can be composed of a number of materials routinely used in the art, including nitrocellulose, polycarbonate, nylon, cellulose acetate, coated cellulose acetate, polyethersulfone, polyester, glass fiber, polyethersulfone, polypropylene, polytetrafluoroethylene (PTFE; Teflon®), polyvinylidenedifloride (PVDF), and copolymers. Typically, membrane mean pore size will be on the order of 0.1 to 5 microns, preferably 1 to 5 micron pore size for retaining protozoa and fungi, and more preferably 0.2 to 0.5 microns for retaining bacteria. Acceptable flow rates are typically greater than 1 liter/minute for gaseous samples and 10 milliliters/minute for liquid samples.

The fluid passes through the membrane and exits through an exhaust chamber around a medium reservoir (FIG. 3). The medium reservoir contains a growth medium that is able to support the growth of a target microorganism. Typically, growth media used in this invention will be complex media that contain nutrients, vitamins, minerals and various other substances that allow for the rapid growth of one or more target microorganisms. The medium reservoir consists of a closed container with at least one seal that can be readily pierced or broken to release the growth medium contained within the medium reservoir. The growth medium within the reservoir will typically be sterile. Examples of growth media that can be used in this invention include general purpose or non-selective media such as nutrient broth, Sabouraud culture media, trypticase soy broth, and brain-heart infusion media. Selective media can be used in the present invention to suppress or inhibit the growth of non-target microorganisms while permitting the growth of target microorganisms. Examples of selective media include those containing antibiotics, dyes such as crystal violet, or azide that inhibit or kill non-target microorganisms. Selective media can also comprise a selective pH or electrolyte concentration. Enrichment media can be used in the present invention to suppress the growth of competitive normal microflora while enhancing the growth of target microorganisms. Examples of enrichment media include media enhanced by addition of bicarbonate to the growth medium for enriching for *Bacillus anthracis* (e.g., 0.8% sodium bicarbonate in the presence of 5% $CO_2$), GN broth, Hajna (e.g., for enrichment of *Shigella* or *Salmonella*), selenite crystal broth (for enriching for *Salmonella*, and tetrathionate broth (for enriching for *Salmonella*). Other specialized isolation media can be used in the present invention, such as, for example, Lowenstein Medium for the selection an enrichment of mycobacterial species.

Figure 6:
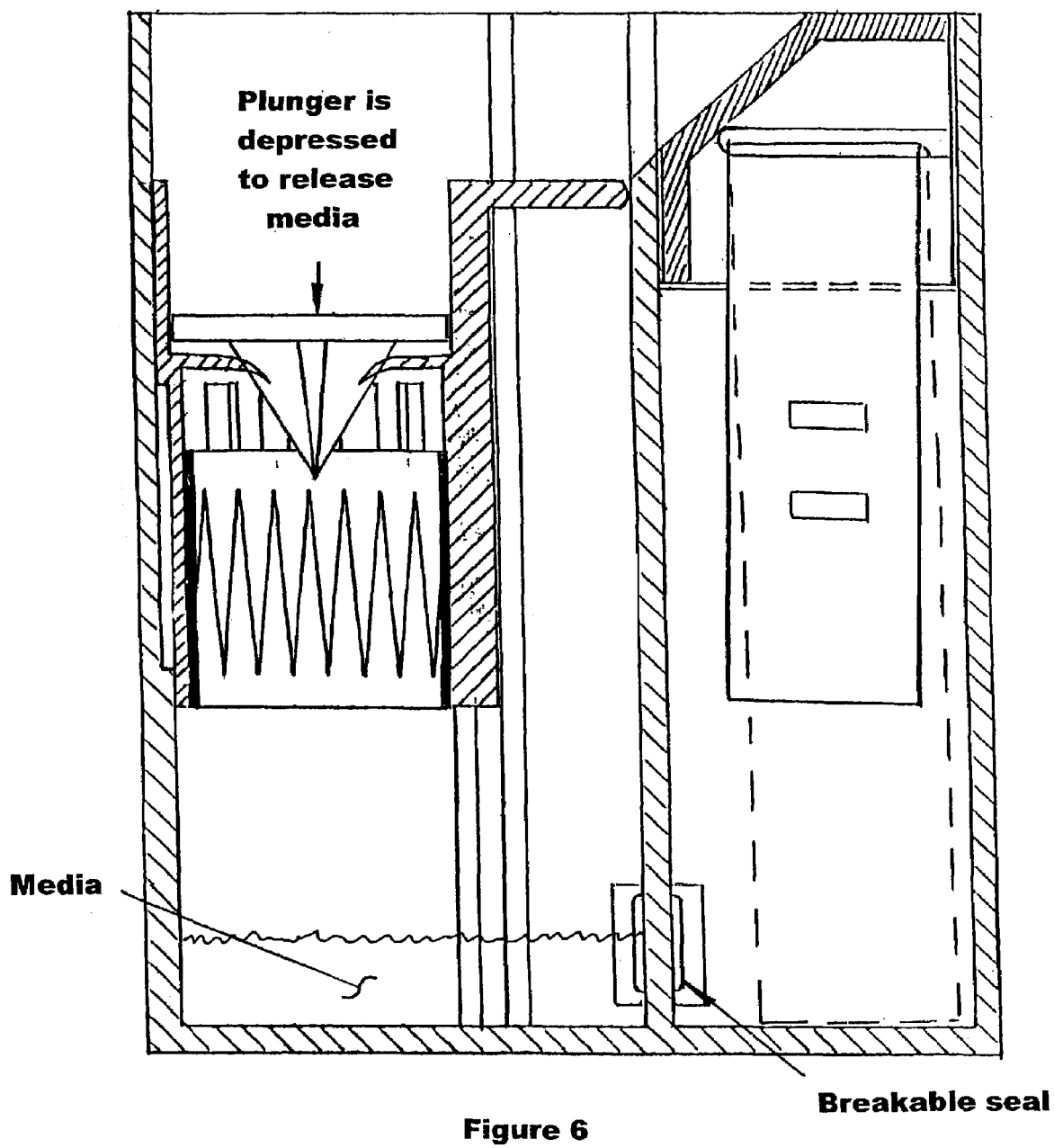
FIG. 6 shows a cross section of the test cartridge after plunger as been depressed forcing the growth medium through the filter into the growth chamber.
Figure 7:
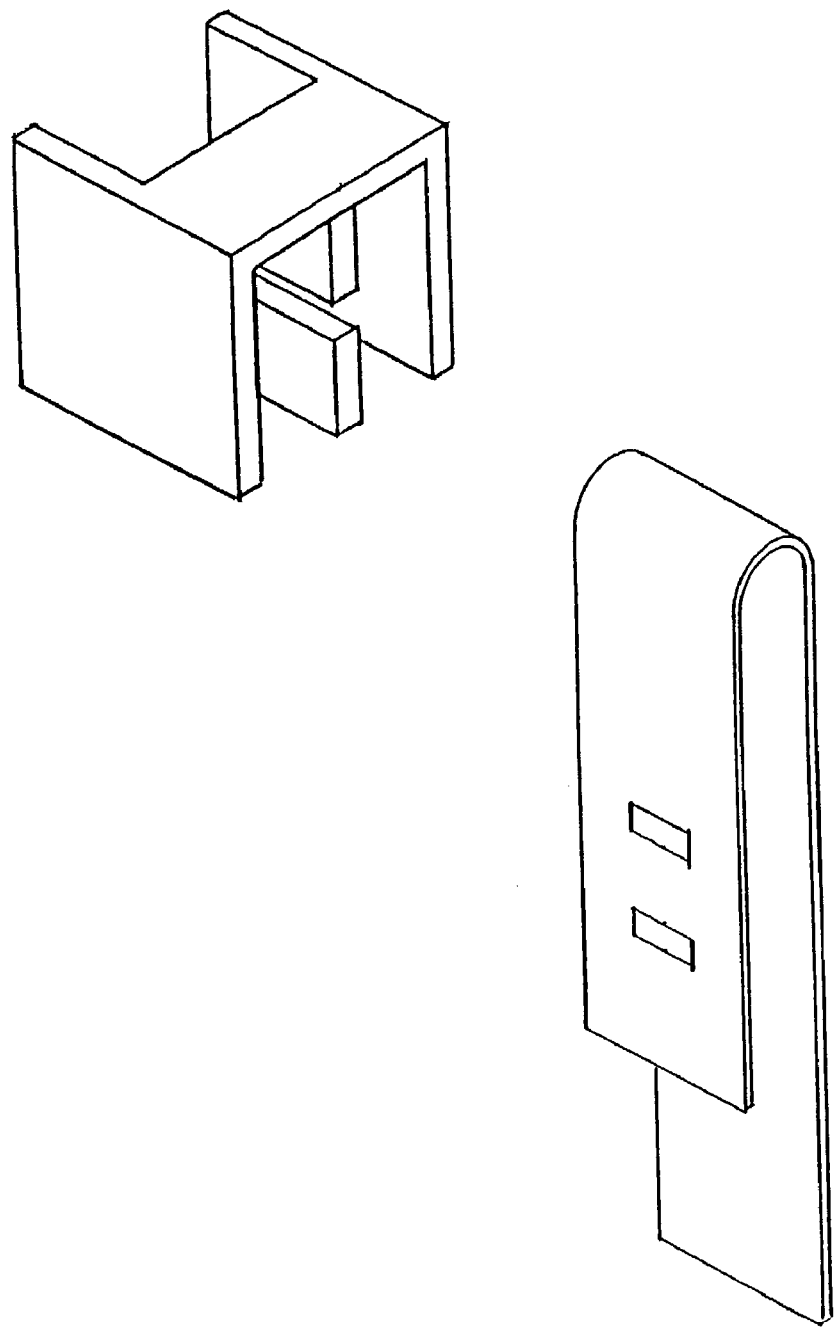
FIG. 7 shows the test strip and its holder.

Test cartridges for liquid or gas sample collection further comprise a plunging means for piercing or breaking a seal of the medium reservoir (FIG. 6). The component has a knife or pointed edge that, when it contacts the medium reservoir seal with sufficient force, pierces or breaks the seal and releases the growth medium. Thus, when the plunger means is depressed, the growth medium is released from the medium reservoir. Depressing the plunger means also and simultaneously engages a seal between the medium reservoir and the semipermeable membrane. In some embodiments, this seal can be hermetic. By the action of the plunger means, the growth medium present in the reservoir is forced through the membrane in a direction opposite of the flow of the fluid sample. This has the effect of backwashing any microorganisms that can be retained on side of the semipermeable membrane opposite the medium reservoir and suspending the microorganisms in the growth medium.

The test cartridge also contains a sample chamber that receives the growth medium from the filter. In a preferred embodiment, microorganisms captured by the membrane are able to grow in the medium, metabolize and produce specific analytes. The movement of the growth medium into the chamber can be generated by pressure, vacuum, electrokinetics, capillary action, gravity, or a combination thereof. A breakable seal is interposed between the sample chamber and a test chamber, the latter containing a means for the detection of the target organism. Movement of fluid from the sample chamber to the test chamber following breakage of the seal between the chambers can be generated by gravity, vacuum, capillary action or other means.

In one embodiment, a sufficient number of target microorganisms are originally present in a fluid specimen that a period of growth and associated biological amplification is not necessary to detect the target microorganisms. In this embodiment, the microorganisms are detected during a first detection assay, as described generally and in specific embodiments below.

The device also comprises a programmable temperature-regulating means that maintains the sample chamber at a temperature that promotes growth of at least one of the target microorganisms that can be present in the growth medium. The growth medium is incubated for a period of time and then assayed for the presence of at least one of the target microorganisms, as described below. Programmable temperature-regulating means used in the monitoring device are well known in the art, and in a preferred embodiment include electric resistive heating elements. The temperature of the chamber is generally adjusted to an optimum or near optimum temperature for growth of one or more of the target microorganisms. Incubation temperatures vary depending on the requirements of the target microorganisms, and are typically within the range of 12° C. to 45° C. The temperature for optimizing growth of *Enterobacteriaceae*, including *Shigella, Escherichia*, and *Salmonella* species, is preferably about 37° C. The temperature for optimizing the growth of *Bacillus anthracis* is preferably about 35° C.

At least one programmable timer is used in the monitoring device to regulate and control the duration of the intervals between assay measurements. At least one timer can be mechanical, and preferably electronic or computer-based. At least one timer can also be variably programmable so that time intervals of various durations can be programmed, such as, for example, one length of time for heat-shocking endospores and another time length of time for incubating microorganisms at an optimum or near-optimum temperature for growth. The time and duration of elevated temperature treatment can vary according to the target microorganism being detected. For example, endospores of *B. anthracis* can be incubated at 65° C. or 75° C. for 20 minutes to induce germination of endospores, although the temperature and duration of the shock period can vary with specific requirements of suspected target strains.

The timer can be used to control intervals between detection assays in the monitoring device; a negative assay result is followed by subsequent round of incubation of the growth medium in the detection unit and another detection assay after a suitable period of time has elapsed. The period of incubation will vary depending on the type of microorganism being detected. The incubation periods for assays for the detection of fast growing species such as *Bacillus anthracis* or *Salmonella* species would typically be of short duration, such as, for example, about 10 to 120 minutes. The incubation periods for the detection of slow growling species such as *Mycobacterium* species are typically of longer duration, and can be from about 1 to 24 hours. The monitoring device can also be manually directed, either at a remote control unit or at the monitoring device, to repeat an incubation period and assay measurement. The incubation allows the unit to determine the presence or absence of a pathogen in the sample in a relatively small amount of time, typically 6 to 24 hours. If no incubation period is required (e.g., if the concentration of pathogen exceeds levels for which incubation is required), the response time of the detection unit may be reduced to as little as 10 minutes.

In embodiments where the test sample is being assayed for presence of a virus, the growth media may include an appropriate viral host organism for bioamplification.

In the case of *Bacillus anthracis*, infected individuals may become severely compromised in as little as 3 days. The 24 hour maximum response time of the detection device allows health care workers to effectively treat patients well before symptoms may become severe or life-threatening.

As microorganisms grow and metabolize, they release or secrete substances that can serve as potential analytes for a detection assay. Examples of such analytes that can be used to identify microorganisms in a protein-based assay include proteins and peptides such as *Bacillus anthracis* toxin, *Yersinia* outer membrane proteins, *Siaphylococcus enterotoxin B, Blastomyces dermatitis*, WI-1 adhesin, *Histoplasma capsulatum* H antigen, and cholera toxin. A test chamber for proteomic-based assays comprises a means for the detection of at least one target microorganism analyte. For example, a single-step enzyme immunoassay can be used for detection. In this embodiment, the testing means includes a strip composed of a adsorptive material that is capable of wicking by capillary action a liquid to a capture and test or indicator region on the detection strip (FIG. 1). The adsorptive material permits the adsorptive transport of the growth medium between the test chamber and the control test regions. When the growth medium from the test chamber moves to the either region, analytes released or secreted by target microorganisms bind to the capture region. The presence of microorganisms in the growth medium in minimally detectable numbers is determined with a detection means in the test chamber. Because a small fraction of the growth medium is removed from the test chamber, the detection means does not significantly affect the volume growth medium, which is available for subsequent incubation and detection assays.

In one embodiment, the sample in growth medium may be preserved for future detection assays. Preservation may be achieved via freezing of the detection unit, isolation of the sample and growth medium for innoculation on petri dishes, or other methods known in the art.

In one embodiment, the detection means of the test chamber comprises monoclonal anti-analyte antibodies bound to a colored pigment. After the seal between the sample chamber and the test chamber is broken, growth medium enters the test chamber and specific microbial analytes that have been generated and/or released into the medium by target microorganisms bind the anti-analyte antibodies on the detection strip. The analyte-pigmented antibody complex contacts the sorptive material of the test strip and, by capillary action, moves to the test and control regions of the strip. In the control region, polyclonal anti-mouse antibody is immobilized on the strip. By virtue of the presence of mouse antibody, mouse antibody: analyte complex binds to the control region and acts as a positive control. The test region of the test strip contains immobilized polyclonal anti-analyte antibodies bound to the strip. By virtue of a specific binding interaction of the bound antibody and analyte, mouse antibody:analyte complex, if present, binds to the immobilized polyclonal anti-analyte antibodies of the test region. An optical sensor (FIG. 8, feature 10), generally located outside of the test chamber, the latter having at least one exterior transparent component, can be used to determine the presence of pigment at the test and control regions of the detection strip. The presence or absence of pigment at the test region is reported to the assay analyzer as a positive or negative result, respectively.

In various other embodiments of the invention, the detection means of the test chamber comprises a method of detecting the presence or absence of a pathogen using fluoresence, colorimetric analysis, radioactive tagging, magnetic tagging, or other detection means known in the art.

The monitoring device can be programmed with a control unit, preferably a computer control unit. The control unit is used to program various assay parameters, including sampling parameters such as quantity, flow rate and duration of sampling, plunger activation, incubation temperatures, incubation periods, incubation chamber seal puncture and number of assay cycles. The control unit can also be used to direct the movement of one or more detection chambers within the monitoring device. The control unit can be built into the monitoring device, can be located in the proximity of the monitoring device, or can be remote. Instructions for the monitoring device can also be transmitted over a computer network. The use of a computer control unit allows a human operator to program initially or change assay parameters as desired or required.

Figure 5:
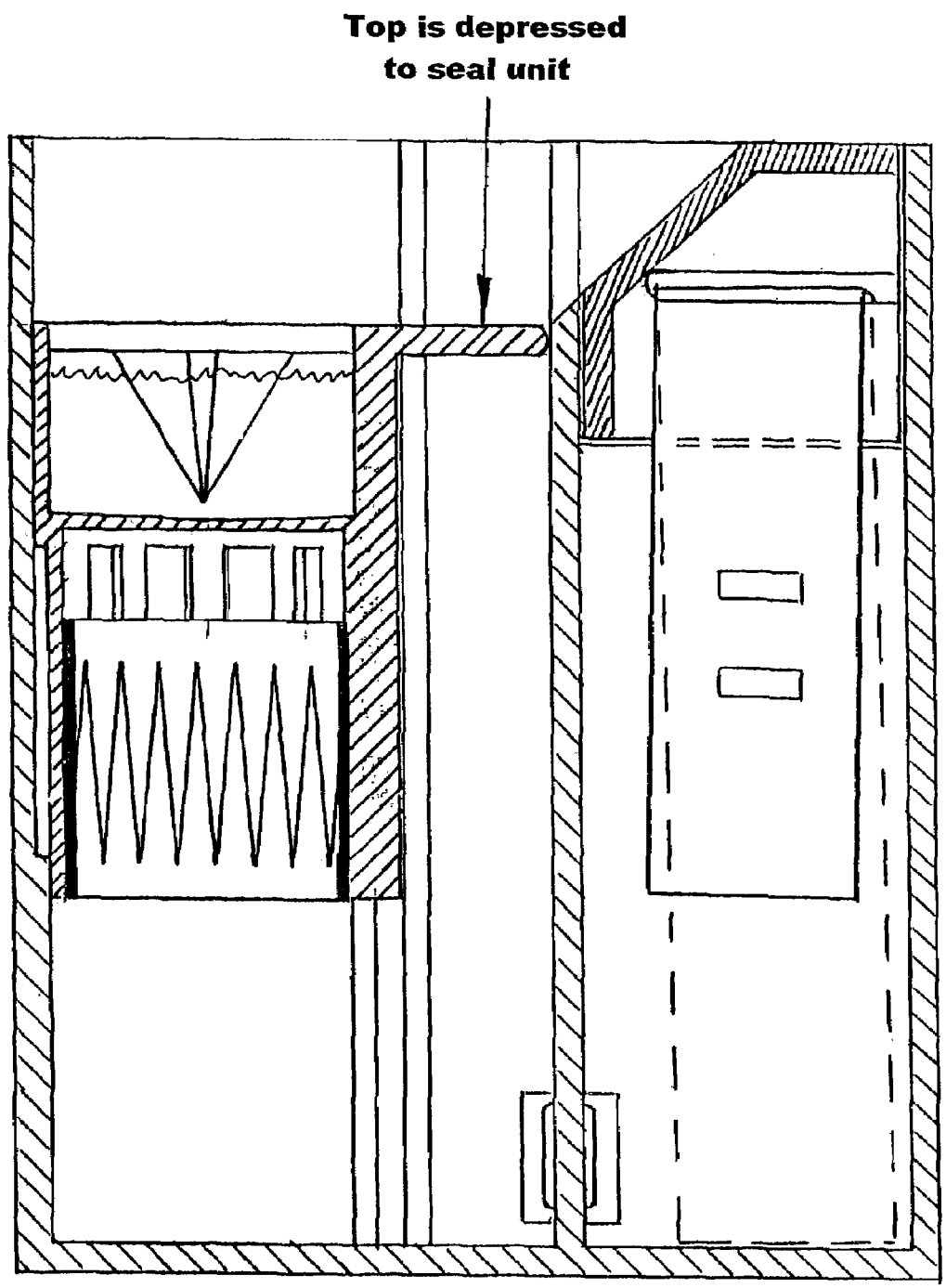
FIG. 5 shows a cross section of the test cartridge following air sampling and sealing.

A preferred embodiment of the monitoring device is shown in FIGS. 1 through 8. The following numbers refer to features on FIG. 8 unless otherwise indicated. A delivery cassette (1) contains test cartridges (2), which are moved to sampling station (5) via a cartridge feed mechanism (3) operably linked to a feed motor (4). An air sample in pulled through the monitoring device using an air intake (6) that directs the airflow through the test cartridge (FIG. 4) and exits the monitoring device through the exhaust (6). A plunging mechanism (7) then seals the test cartridge (FIG. 5). The plunger then depresses the growth media cartridge which releases the media through the collection filter (FIG. 6) and into bottom of the sample chamber. Test cartridges are moved to an incubation station (9) which holds each test cartridge at a temperature appropriate for the growth of the target organisms. The temperature within the incubation station is controlled with a heat control card (9). After a programmed incubation period, a breakable seal (FIG. 4) is pierced and growth medium enters a test chamber (FIG. 4). The medium moves up a detection strip (FIG. 1) within the test chamber and past the indicator and control regions of the detection strip (FIG. 4), at which antibody:analyte complexes will bind. Multiple detection strips can be placed in the same cartridge. After the detection strip assay is performed within the test chamber, results are detected by the result sensor (10). The test cartridge is subsequently moved to the outgoing cartridge position holder (11) then by the cartridge ejector solenoid (12) into the biowaste cassette (13). Means for transmitting programmed instructions from the control unit to a remote monitoring device include wire connection, a radio link, phone lines, microwave transmission, infrared transmission, a cellular phone, or a computer network.

Figure 11:
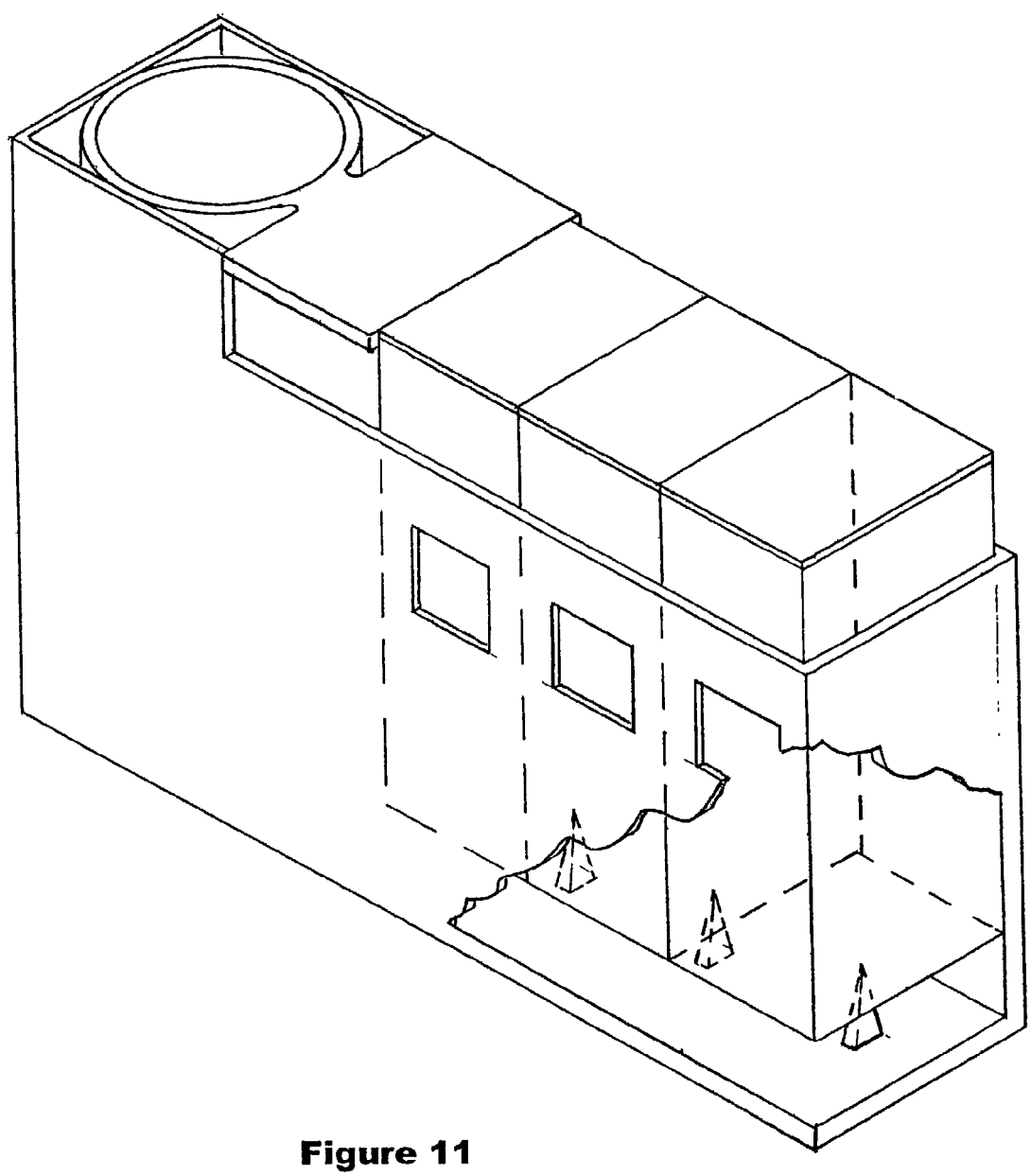
FIG. 11 shows another embodiment of the test cartridge with multiple detection strips.
Figure 12:
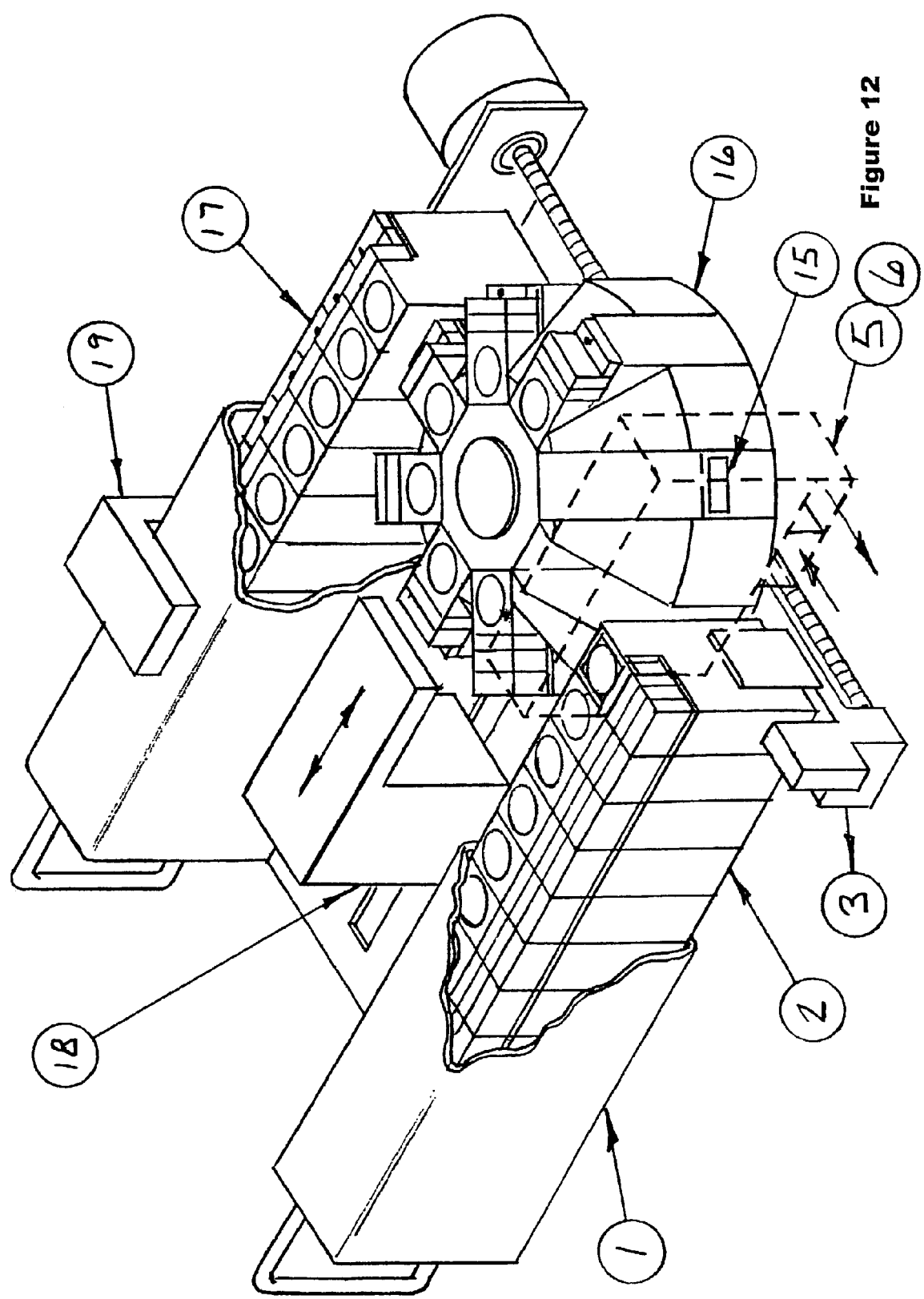
FIG. 12 shows another embodiment of the automated system that moves, heats, times, senses changes in, records data from multiple test cartridges running concurrently and stores the test cartridges. Numbered parts as follows: 1—Delivery cassette, 2—Incoming cartridge, 3—Cartridge feed mechanism, 5—Sampling station, 6—Air intake and exhaust, 16—Carousel, 17—Cartridge with one test left, 18—Plunge and read station, 19—Plunge and read station for 3rd test.

In another preferred embodiment of a test cartridge operating device, the device can test a plurality of test cartridges concurrently (FIG. 12). FIG. 12 demonstrates a device capable of heating, incubating, and sensing test results from 8 test cartridges. Each of the test cartridges shown in this example has 3 testing chambers (FIG. 11), with breakable seals at the base of the testing chambers and a non-opaque window for viewing test results on the side or the top of the chamber. These chambers can be used to test samples at different time points or detection strip tests that are incompatible for concurrent testing.

Assay results, i.e., the presence or absence of target microorganisms, can be displayed at the device but preferably are reported to a remote assay analyzer. Typically, the assay analyzer is a computer or microcomputer and preferably is the same computer or microcomputer functioning as the control unit. The assay analyzer is used for both signal processing and data storage. Means for transmitting assay results from the monitoring device to an assay analyzer include wire connection, a radio link, phone lines, microwave transmission, infrared transmission, a cellular phone, or a computer network. The assay results can also be transmitted over a computer network.

If more than one monitoring device is used, any one device can identify its location to the assay analyzer with positional information derived from manual data entry or, preferably, from a global positioning means that automatically communicates the latitude and longitude coordinates of the monitoring device. The positional information can be communicated to the assay analyzer via wire, microwave, radio, or cellular telephone transmission, and can be transmitted along with assay results. The assay analyzer is capable of storing and reporting location information for all of the monitoring devices used within a defined geographical region being tested for the presence of microorganisms. Limitations as to the number of monitoring devices communicating with a single assay analyzer, and the size of the geographical region being tested, are determined by computer's power and data storage capacity, and transmission means, respectively. Given the capacity of today's computers to process and store large quantities of data and transmit data at high speeds, it is anticipated that a large number of individual monitoring devices can be linked to a single assay analyzer. In regions where data transmission factors limit the number or distribution of monitoring devices, multiple networks of device, each network having a single assay analyzer, can be employed. In the latter case, and where data transmission is via radio or microwave, monitoring devices and control units can also transmit a registration signal to avoid "crosstalk" between different networks of devices.

For any one monitoring device, assay results are reported to the assay analyzer as a positive result, i.e., a target microorganism is present in at least one test chamber, or as a negative result, i.e., no target microorganism has been detected in a given test chamber. The assay analyzer can also have the ability to determine and update the status of any and all monitoring devices with which it is communicating. In this embodiment, the monitoring device signals the assay analyzer, either after a query or at regular intervals, that the monitoring device is performing within specified parameters. The monitoring device can be equipped with sensors that report internal temperature settings, plunger activation and fluid and detection unit movement.

Prior to, the termination of assay measurements, the reporting of a negative result to the assay analyzer can prompt a subsequent round of incubation of the growth medium and a subsequent detection assay. Any one monitoring device can contain a plurality of detection units for performing additional detection assays after negative results with one detection unit are reported to the assay analyzer. In one embodiment, fluid specimens are similarly passed through multiple test units rather than a single test unit. Following a prescribed incubation period and negative assay result within a first test unit, the breakable seal between the incubation chamber and the test chamber of a second test unit can be pierced and a second detection assay performed. This cycle can be repeated until such time as a positive result is reported, or all detection units through which the fluid specimens passed have been used, or a period of time has elapsed without positive detection that suggests that no target organism existed in any of the fluid specimens. In a second embodiment, a single monitoring device can be used in a detection assay for one fluid or swab specimen, after which the detection units used in that determination are disposed, and new detection units are moved into place to detect microorganisms in a distinct specimen. In this manner, the detection device reduces or eliminates the occurrence of false positives or false negatives via the ability to repeat detection tests at a given location.

Because each monitoring device contains a plurality of detection units, each monitoring device can also be used to assay distinct fluid specimens. After any detection unit within a monitoring device has been inoculated and assayed, separate detection units can be inoculated with fresh fluid specimens derived from air, liquid or swab samples.

In one embodiment, the plurality of detection units may each be directed towards the detection of a specific pathogen different from the pathogens detected by the other units in the plurality. In this way, the plurality may be used to detect the presence or absence of several different microorganisms at one location.

In another embodiment, the plurality of detection units may all be directed towards the same pathogen (e.g. anthrax). In this way, the plurality may be used to detect the presence or absence of one pathogen at many locations, or may use a self-checking mechanism of repeatedly testing for one pathogen at the same location.

Due to the small size and low energy requirements of an individual monitoring device, the device can be made portable. For portable units, location information is preferably determined by global positioning means and transmitted to the assay analyzer via microwave, radio, or cellular telephone transmission.

The invention is also directed to methods for detecting pathogens in an air or fluid specimen. These methods include passing a fluidic sample, such as a gas or liquid specimen, through the pathogen monitoring system described herein. Microorganisms that are present in the sample are retained on a semipermeable membrane. The microorganisms are incubated in a growth medium suitable for at least one target microorganism that can be present in the specimen at a temperature appropriate for growing at least one of the target microorganisms. The presence or absence of target microorganisms is determined with a detection means within the pathogen monitoring system. A negative result, that is, failure to detect a target microorganism in any one detection assay, prompts a subsequent round of medium, incubation and detection assay, until such time that one or more target microorganisms are detected, or after a sufficient period has elapsed in which one or more target microorganisms would have grown to detectable numbers if present in the specimen.

The invention is also directed to a kit for detecting microorganisms. The kit comprises at least one disposable cartridge for use in the microbial monitoring system disclosed herein, and at least one sterile container for retaining the disposable cartridges. Kits typically include a label indicating the intended use of the contents of the kit. The term label includes any writing, or recorded material supplied on or with the kit, or which otherwise accompanies the kit.

The invention is also directed at early detection of pathogenic contamination. Automated monitoring devices can be installed in a wide variety of locations such as post offices, commercial centers, government buildings, airplanes, transportation centers (i.e., airports, bus terminals, train stations, and shipping docks and alike), and other locations suspected of being likely targets of bioterrorism. These devices can be programmed to run a test using an appropriate test cartridge at predetermined intervals. Results from these tests, along with device location information, can be sensed and reported to the appropriate agency. Appropriate agencies can include Centers For Disease Control and Prevention, Office of Homeland Security, medical professionals, and hazardous response teams.

EXAMPLES

Example 1

Analysis of Manually Collected Samples for *Bacillus anthracis* Spores

Figure 10:
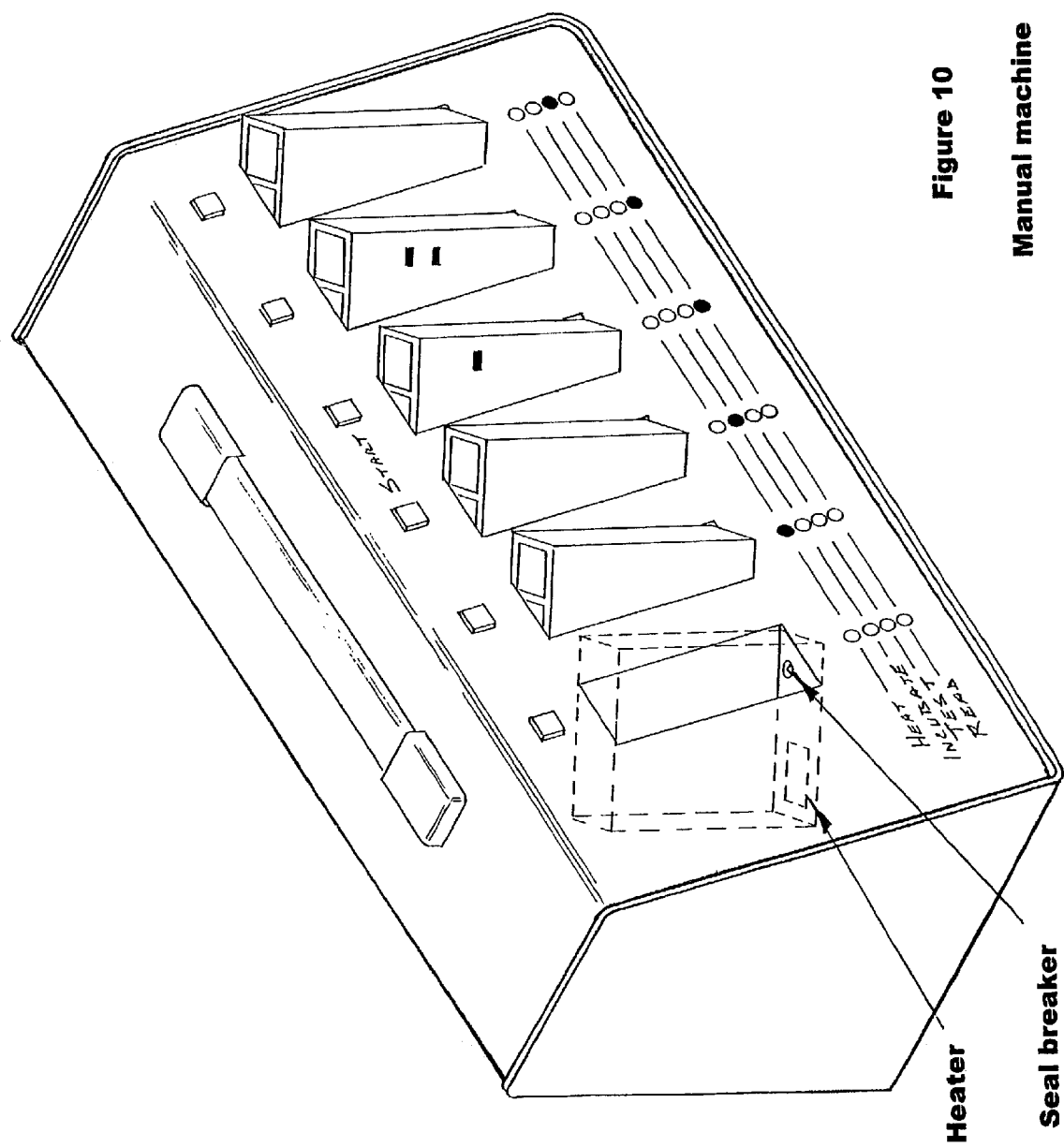
FIG. 10 shows a portable device for testing six manually loaded cartridges.

This example illustrates the use of a device such as that represented in FIGS. 9 and 10. First, surfaces to be examined for the presence of *Bacillus anthracis* should be wiped with an appropriate collector such as a cotton swab or a small filter. The collector should then be placed in the side of the cartridge that will receive the growth media insert as illustrated in FIG. 9, such that the collector rests below the 'Fill to Here' line indicated on the drawing. The growth media and detection strip inserts should be placed into the cartridge, and the cartridge loaded into a slot of the device shown in FIG. 10.

In this case, we are testing for *Bacillus anthracis* spores. The media should be appropriate for the germination of spores followed by growth, such as CA broth (Thorne and Belton, 1957, J. Gen. Microbiol. 17:505-516) supplemented with 20 ug/ml tryptophan and buffered with 100 mM HEPES pH 8.0 (Dai and Koehler, 1997. Infection and Immunity 65:2576-82). The program for the machine should be set to heat shock the collected spores for 20 minutes at 65° C., followed by a reduction in temperature to 37° C. to allow for growth of bacteria. Incubation at 37° C. should continue for two hours or for a length of time such that the number bacteria produce enough toxin to be above the detection limit of the detection strip.

At the end of the bacterial growth stage, the device of FIG. 10 will break the breakable seal between the chambers of the cartridge (FIG. 9). The bacterial suspension will then flow into the chamber containing the detection strip specific for an element of *Bacillus anthracis*. Once in contact with the detection strip, the suspension will be wicked up the length of the strip past the indicator and control lines. This process should take approximately 3-5 minutes. The results will be analyzed by the result sensor, which will compare the indicator line to the positive control. If the indicator line and the control line are positive, the test will indicate the presence of *Bacillus anthracis* spores in the collected sample. If the indicator line is negative and the positive control line is positive, then no *Bacillus anthracis* spores were collected in the sample. If the positive control line is negative for any reason, the test is designated as a failure and should be repeated.

Results from this test will be displayed as appropriate for the situation. This could be through digital or printed results displayed at the device, or through an integrated communication system such as a cell phone to a remote computer. In another aspect, a coupled GPS receiver could identify the location of the unit upon initiation of the sample testing, and communicate this information as well.

Example 2

Analysis of Air Samples for *Bacillus anthracis* Spores

Figure 8:
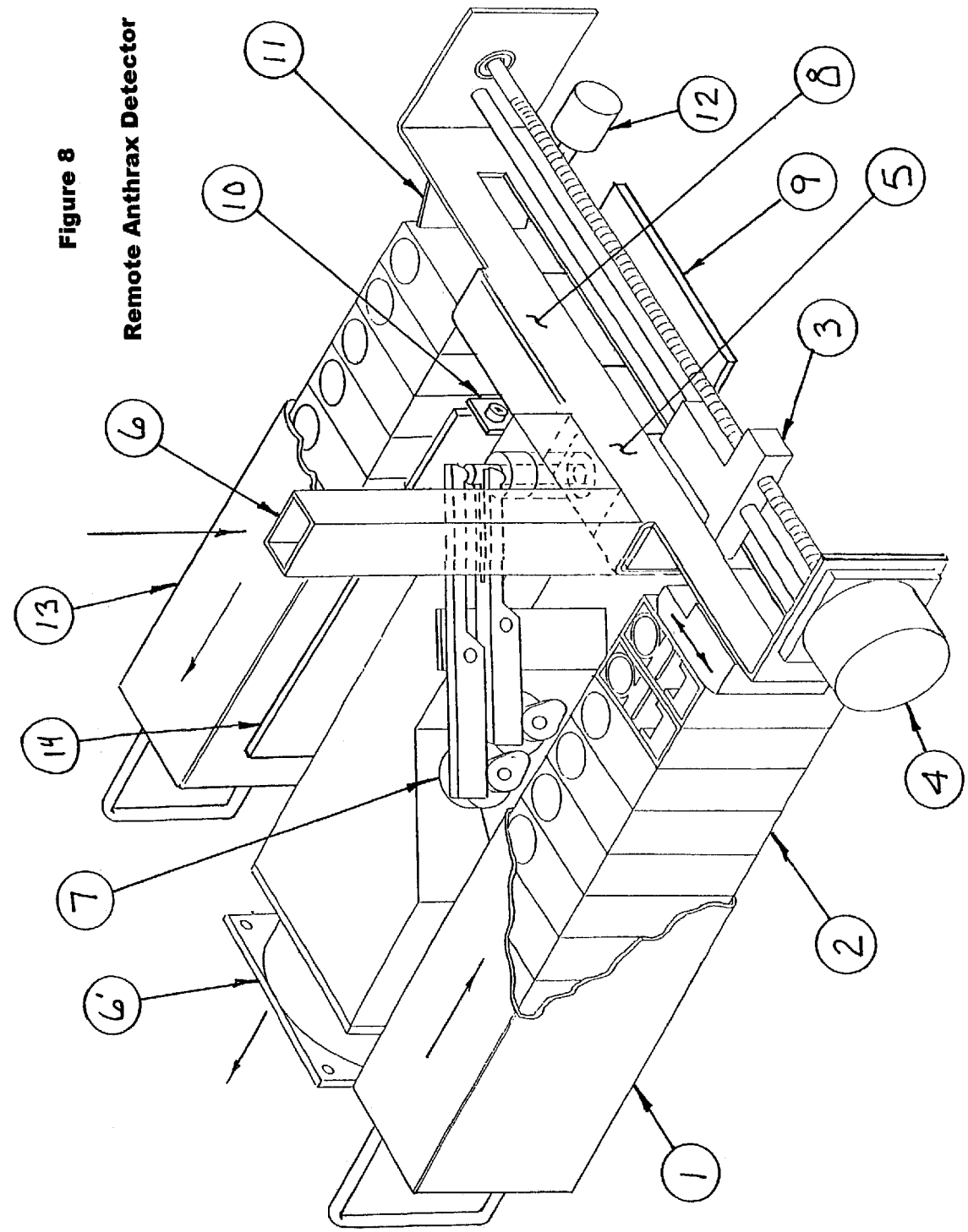
FIG. 8 shows one embodiment of the automated system that moves, heats, times, senses changes in, records data from and stores the test cartridges. Numbered parts as follows: 1—Delivery cassette, 2—Incoming cartridge, 3—Cartridge feed mechanism, 4—Feed motor, 5—Sampling station, 6—Air intake, 6'—Air exhaust, 7—Plunging mechanism, 8—Incubation station, 9—Heat control card, 10—Result sensor card, 11—Outgoing cartridge position holder, 12—Cartridge ejector solenoid, 13—Biological waste cassette, 14—Microcontroller card.

This example illustrates the use of a device such as that represented in FIG. 8 using cartridges such as that shown in FIGS. 1 through 7. The device can be placed in any upright position such that the inlet (6) and outlet (8) of FIG. 8 are not obstructed and have air access. Cartridges specific for detection of elements of *Bacillus anthracis* should be loaded into the delivery cassette (FIG. 8-1). The machine can be programmed to activate a detection run either remotely or on a schedule.

Upon activation of a run, a test cartridge is moved into the sampling station (FIG. 8-5) by the cartridge feed mechanism (FIG. 8-3). The fan (FIG. 8-6') is activated and air is pulled through the cartridge (see FIG. 3) from the air inlet (FIG. 8-6) and exhausted through the exhaust port (FIG. 8-6'). Approximately 15 liters of air should be pulled through the cartridge (equivalent to 2 people breathing for 1 minute). This can be increased to sample larger areas. After collection of particulates from air, the Plunging mechanism (FIG. 8-7) is activated to release the growth media from the growth media reservoir (FIG. 1) and force it through the filter, eluting particulate matter from the filter. In this case, we are testing for *Bacillus anthracis* spores. The media should be appropriate for the germination of spores followed by growth, such as CA broth (Thorne and Belton, 1957. J. Gen. Microbiol. 17:505-516) supplemented with 20 •g/ml tryptophan and buffered with 100 mM HEPES pH 8.0 (Dai and Koehler, 1997, Infection and Immunity 65:2576-82).

The cartridge is then moved by the cartridge feed mechanism (FIG. 8-3) to the incubation station (FIG. 8-8). The program for the machine should be set to heat shock the collected spores for 20 minutes at 65° C., followed by a reduction in temperature to 37° C. to allow for growth of bacteria. Incubation at 37° C. should continue for two hours or for a length of time such that the number bacteria produce enough of the element assayed to be above the detection limit of the detection strip.

At the end of the bacterial growth stage, the device of FIG. 8 will break the breakable seal between the chambers of the cartridge (FIG. 4). The bacterial suspension will then flow into the chamber containing the detection strip specific for an element of *Bacillus anthracis*. Once in contact with the detection strip, the suspension will be wicked up the length of the strip past the indicator and control lines. This process should take approximately 3-5 minutes. The results will be analyzed by the result sensor (attached to FIGS. 8-10), which will compare the indicator line to the positive control. If the indicator line and the control line are positive, the test will indicate the presence of *Bacillus anthracis* spores in the collected sample. If the indicator line is negative and the positive control line, is positive, then no *Bacillus anthracis* spores were collected in the sample. If the positive control line is negative for any reason, the test is designated as a failure and should be repeated. After the results have been collected, the cartridge is moved to the Biological Waste cassette (FIGS. 8-13) to store the cartridge for either re-testing or disposal.

Results from this test will be displayed as appropriate for the situation. This could be through digital or printed results displayed at the device, or through an integrated communication system such as a cell phone to a remote computer. In another aspect, a coupled GPS receiver could identify the location of the unit upon initiation of the sample testing, and communicate this information as well.

It is understood that the examples and embodiments described herein are for illustrative purposes only and that various modifications or changes in light thereof will be suggested to persons skilled in the art and are to be included within the spirit and purview of this application and scope of the appended claims.

All publications, patents and patent applications cited herein are hereby incorporated by reference in their entireties for all purposes to the same extent as if each individual publication, patent or patent application were specifically and individually indicated to be so incorporated by reference.

What is claimed is:

1. A cartridge for detecting microorganisms, comprising:
   an intake or receptacle through which a fluid or a gas enters said cartridge or is added to said cartridge;
   a filtering means through which said fluid or gas passes and retains microorganisms present in said fluid or gas;
   an exhaust chamber, wherein said filtering means is interposed between said intake or receptacle and said exhaust chamber;
   a medium reservoir on a side of said filtering means opposite said retained microorganisms, comprising a microbial growth medium and a reservoir breakable seal;
   a plunger means, wherein pressure placed on said plunger means:
   (i) engages a hermetic seal between said medium reservoir and filtering means;
   (ii) breaks said reservoir breakable seal and forces growth medium through said filtering means in a direction opposite of flow of said fluid or gas; and
   (iii) backwashes said microorganisms from said filtering means and suspends said microorganisms in said growth medium;
   an incubation chamber for incubating and growing said microorganisms;
   a thermally conductive surface for controlling the temperature of said incubation chamber;
   an incubation chamber breakable seal through which said growth medium passes into a test chamber for detecting said microorganisms;
   a detection means within said test chamber; wherein
   said detection means determines the presence or absence of said microorganism without killing said microorganisms or inhibiting said growth; and
   a transmission means; wherein said presence or absence of said microorganism is reported via said transmission means to an assay analyzer.

* * * * *